United States Patent [19]

Warner

[11] 3,994,979

[45] Nov. 30, 1976

[54] DISULFIDE PROCESS

[75] Inventor: Paul F. Warner, Phillips, Tex.

[73] Assignee: Phillips Petroleum Company, Bartlesville, Okla.

[22] Filed: May 1, 1975

[21] Appl. No.: 573,489

[52] U.S. Cl. ................................................ 260/608
[51] Int. Cl.² ...................................... C07C 149/12
[58] Field of Search ..................................... 260/608

[56] References Cited
UNITED STATES PATENTS

| | | | |
|---|---|---|---|
| 2,001,715 | 5/1931 | Fischer | 260/608 |
| 3,340,324 | 4/1965 | Warner | 260/608 |
| 3,397,244 | 8/1968 | Louthan | 260/608 |

Primary Examiner—Elbert L. Roberts
Assistant Examiner—D. R. Phillips

[57] ABSTRACT

Disulfides are produced in high yields and high purity by a process comprising first converting thiols to alkali metal mercaptides by treatment with an alkali metal hydroxide in a reaction medium comprising N-methylpyrrolidone, N-methylpyrrolidone/water, and isopropanol/water and then reacting the mercaptide with elemental sulfur in the reaction medium to form the disulfide.

8 Claims, No Drawings

DISULFIDE PROCESS

This invention relates to the production of organic disulfides. In accordance with another aspect, this invention relates to the stepwise production of organic disulfides which are produced in increased yields and high purity by carrying out the reaction in a reaction medium comprising N-methylpyrrolidone or water and N-methylpyrrolidone or isopropanol. In accordance with a further aspect, this invention relates to the improved process for the production of organic disulfides by converting mercaptans to alkali metal mercaptides in a reaction medium comprising N-methylpyrrolidone or isopropanol and then converting the mercaptides to disulfides by reaction with sulfur.

A wide variety of organic disulfides are known, some of which have wide utility. However, the processes currently available for preparing these compounds are so tedious and expensive that the price of these compounds has remained relatively high, thus preventing real commercial development. It has been found that organic disulfides in good yields and in high purity can be produced by converting thiols to mercaptides and then to disulfides provided the reactions are carried out in a reaction medium comprising N-methylpyrrolidone or isopropanol.

Accordingly, it is an object of this invention to provide a new and improved process for making organic disulfides.

Another object of this invention is to provide an improved process for producing high yields of high purity organic disulfides.

Other aspects, objects, and the several advantages of the invention will be apparent to those skilled in the art upon a reading of the specification and the appended claims.

According to the invention, thiols are converted to alkali metal mercaptides by reaction with an alkali metal hydroxide in a reaction medium comprising N-methylpyrrolidone or isopropanol and then the resulting mercaptides in the reaction medium are converted to the corresponding disulfides by reaction with sulfur.

Quite surprisingly, it has been found that mercaptans can be converted directly to disulfides with sulfur without going through the tri- and polysulfides if the mercaptan is first converted to the alkali metal mercaptide in a reaction medium comprising N-methylpyrrolidone or isopropanol.

The initial reaction is the formation of the alkali metal mercaptide:

$$RSH + MOH \rightarrow RSM + H_2O.$$

M can be any alkali metal, Li, Na, K, Rh, Cs, but Na is preferred because of its ready availability and economy.

In the second step the mercaptide is oxidized by elemental sulfur to the disulfide:

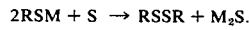

$$2RSM + S \rightarrow RSSR + M_2S.$$

The reaction medium is N-methylpyrrolidone, N-methylpyrrolidone/water, preferably about 50/50, isopropanol/water, preferably about 50/50. The amount of organic material and water in the mixed reaction medium systems is on a weight percentage basis. Since the mercaptides which are formed are insoluble, sufficient reaction medium is used to maintain the weight percent solids below about 35 percent, preferably between 25–30 weight percent.

The reaction is applicable to aliphatic or cycloaliphatic mercaptans as starting materials of the general formula RSH in which R is an alkyl or cycloalkyl radical of 1–20 carbon atoms; specific examples include methanethiol, ethanethiol, 2-methylethanethiol, butanethiol, 2-methylpropanethiol, 2-butanethiol, 2-methyl-2-propanethiol, octanethiol, decanethiol, dodecanethiol, tetradecanethiol, hexadecanethiol, eicosanethiol, cyclobutanethiol, cyclooctanethiol, cyclodecanethiol, cyclododecanethiol, cyclotetradecanethiol, and cyclohexadecanethiol.

As indicated hereinbefore, the instant process results in the production of increased yields of high purity disulfides. In the specific working examples hereinbelow, the reaction is illustrated using tert-butyl mercaptan (2-methyl-2-propanethiol) because the product tert-butyldisulfide, is commercially significant.

The conditions for the reactions of this invention can vary widely, depending upon the materials employed, the yield desired, and the like, the primary requirement being that the reaction is carried out for a length of time sufficient and at a reaction temperature sufficient to cause the final product to contain a substantial preponderance of disulfide relative to other sulfides. Generally, the temperature can be adjusted to vary the reaction time to meet a desired period of time and will vary from about 65° to about 300° F (18.3°–149° C), preferably from about 100° to about 220° F (37.8°–104° C). In a more preferred mode of operation, the temperature is maintained at the reflux temperature. The pressure can also vary widely, depending upon various parameters, but will generally be from about ambient pressure to about 100 psig, preferably from about 3 to about 20 psig. The reaction time can vary from a few minutes to several hours, and generally will be in the range of about 1 to 8 hours.

The reactions can be carried out batchwise or in a continuous operation. At the completion of the reaction the reaction mixture is generally cooled from the reaction temperature, filtered to remove alkali metal sulfide and other impurities, and then treated by such processes as distillation, extraction, and the like for the recovery of the disulfide product. The reaction medium can be recovered and recycled for reuse in the process.

The following specific examples are illustrative of the advantages of the process of the invention which is generally applicable as herein stated.

SPECIFIC EXAMPLES

The runs were made in 2- and 3-liter reaction flasks equipped with mechanical stirrer, reflux condenser, heating mantle, and thermowell. Usually the runs were made at the reflux temperature of the mixture so that a temperature controller was not needed.

Tertiary butyl mercaptan was used in all of the runs. The mercaptan used was slightly off specification in that it contained 5.9 weight percent disulfide.

A commercial grade of sulfur flowers was used. The other reagents were all technical grade or higher in purity.

In most of the runs the reaction medium and sodium hydroxide were charged first with the stirrer running. Then the mercaptan was fed to the mixture at a rapid rate — usually not more than 5–10 minutes were required. There was a slight increase in temperature of about 5°–10° F during the addition. After a few minutes the sulfur was added; there was never any increase in temperature noted on addition of the sulfur to the mercaptide. Heat was now applied and the mixture was raised to the reflux temperature as rapidly as possibly and held at that temperature until the reaction was complete. The time required was dependent to a large degree on the reflux temperature. The reaction mixture usually turned from yellow-orange to greenish-black as the reaction progressed. The disulfide phase, however, was always essentially colorless.

When the reaction was complete, as indicated by analysis of the organic phase by chromatograph, the mixture was transferred to a separatory funnel.

The heavy phase containing sodium sulfide, water, and reaction medium was drawn off and worked up or discarded as described later. On occasion, it was analyzed to determine how much disulfide it contained.

The lighter phase containing the disulfide was analyzed, then was washed with water, or distilled as the case might be. A one-plate vacuum flash unit was used for the distillations.

EXAMPLE I

In Run 1, N-methylpyrrolidone (NMP) and mercaptan were charged originally, and after a few minutes was followed by sulfur addition. No NaOH was used. After 3½ hours at the reflux temperature 160° F (71° C), the reaction mixture contained no disulfide. Trisulfide and polysulfides were the only products, and half of the mercaptan remained unreacted.

EXAMPLE II

NMP and NaOH were charged to the reactor at room temperature and the mercaptan was added rapidly with stirring. This required about 10 minutes and the formation of mercaptide was virtually instantaneous. Sulfur was then added and the mixture was brought to reflux temperature 160° F (71° C) and held for about one hour. Then 500 ml water was added and the reaction mixture was heated and stirred, at reflux (about 200° F), for another hour. Analysis of the disulfide phase showed almost complete conversion of the mercaptan to disulfide with less than 2 weight prcent trisulfide.

EXAMPLE III

Using the procedure of Example II, Run 3 was made with a 50/50 weight mixture of water and NMP. After 1.2 hours, the crude product contained 92 percent disulfide and 3 percent each of unreacted mercaptan and trisulfide. The temperature ranged from 168°–219° F (75.4°–103.9° C) during the reactions. The yield was 86.0 mole percent.

EXAMPLES IV – VI

Three additional runs were made to explore the ratio of NMP to water and the amount of solvent needed. In Run 4 the water/NMP weight ratio was 3/1. The product composition, however, showed that more than 10 percent trisulfide was made. This confirms the earlier experience that when water is used as the sole solvent, trisulfide is the major product.

Runs 5 and 6 were made with decreasing amounts of solvent and to explore the effect of adding excess sulfur. The yield and purity of disulfide were good in both runs. The excess sulfur in amount up to 10 mole percent did not appear to be deleterious. The mercaptide slurry was barely stirrable in Run 6 where the mercaptide comprised about 36 weight percent of the mixture.

Table I presents data for Runs 1–6 carried out as described in Examples I–VI.

TABLE I

DISULFIDE BY THE SULFUR PROCESS WITH N-METHYLPYRROLIDONE OR N-METHYLPYRROLIDONE AND WATER AS REACTION MEDIUM

| Run | No. | 1 | | 2 | | 3 | | 4 | | 5 | | 6 | |
|---|---|---|---|---|---|---|---|---|---|---|---|---|---|
| A. | Solvent, g | | | | | | | | | | | | |
| | NMP | 500 | | 500 | | 600 | | 300 | | 500 | | 400 | |
| | Water | — | | — | | 600 | | 900 | | 500 | | 400 | |
| B. | Conditions | | | | | | | | | | | | |
| | Temperature, °F | 100–160 | | 160–210 | | 168–219 | | 155–205 | | 165–220 | | 165–210 | |
| | °C | 37.8–71 | | 71–99 | | 75.4–103.9 | | 68.8–95.8 | | 73.8–104 | | 73.8–99 | |
| | Reaction Time, Hrs. | 3.5 | | 2.3 | | 1.2 | | 5.0 | | 1.5 | | 3.0 | |
| C. | Charge | g | moles | g | moles | g | moles | g | moles | g | moles | g | moles |
| | NaOH | — | — | 80 | 2.0 | 200 | 5.0 | 200 | 5.0 | 200 | 5.0 | 200 | 5.0 |
| | t-Butyl mercaptan | 180 | 2.0 | 180 | 2.0 | 360 | 4.0 | 360 | 4.0 | 360 | 4.0 | 360 | 4.0 |
| | Sulfur | 32 | 1.0 | 32 | 1.0 | 64 | 2.0 | 64 | 2.0 | 70.4 | 2.2 | 67.2 | 2.1 |
| D. | Recovery of crude prod.,g | — | | 128 | | 306 | | 297 | | 317 | | 302[b] | |
| | Yield based on Mercap.Chg. | — | | 72 | | 86 | | 83 | | 89 | | 85 | |
| E. | Composition of Crude,[a] Wt. % | | | | | | | | | | | | |
| | Lights | 4.8 | | 0.1 | | tr | | tr | | 0.1 | | 0.1 | |
| | t-Butyl Mercaptan | 46.8 | | 1.4 | | 3.1 | | 3.6 | | 0.0 | | 0.2 | |
| | Unidentified | 2.8 | | 1.4 | | 0.9 | | 5.0 | | 0.3 | | 0.6 | |
| | Di-tert-Butyl Disulfide | 0.0 | | 95.5 | | 92.0 | | 80.6 | | 96.8 | | 97.7 | |
| | Unidentified | 0.0 | | tr | | 0.8 | | 0.2 | | 0.1 | | 0.1 | |
| | Di-tert-Butyl Trisulfide | 38.3 | | 1.6 | | 3.0 | | 10.6 | | 2.7 | | 1.3 | |
| | Polysulfides | 7.3 | | 0.0 | | 0.2 | | tr | | — | | — | |
| | Total | 100.0 | | 100.0 | | 100.0 | | 100.0 | | 100.0 | | 100.0 | |

[a]-Actually area percent by chromatography.
[b]-The water-NMP-$Na_2S$ phase contained crystals.

EXAMPLE VII

Isopropanol-water solutions were tried along with several other solvents. Table II presents data for Runs 7 and 8 with isopropanol and water.

In Run 7 the sodium mercaptide was formed in a 50/50 mixture of isopropanol and water, then the sulfur was added. The reflux temperature of the mixture started at 155° F (68.8° C); in a few minutes it went to 170° F (77° C) and remained there for the rest of the run. Samples were withdrawn of the lighter phase periodically and analyzed by chromatograph. The data are shown for samples taken after 2, 4, and 8.5 hours reaction time. An interesting facet of this solvent system is that the isopropanol, for the most part, concentrates in the disulfide phase as indicated by the analyses. Another interesting observation was that both the mercaptan and trisulfide were being depleted throughout the run.

After 8.5 hours reaction time, the reaction mixture was transferred to a separatory funnel; phase separation was good. The organic phase, 863 g, was charged to a one-plate vacuum distillation apparatus and taken to a kettle temperature of 250° F (121° C) at 685 mm Hg absolute (1-atmosphere); this removed essentially all of the isopropanol. A composite of this overhead fraction, 640 ml, 516 g had the following composition:

| | |
|---|---|
| Isopropanol | 93 |
| tert-Butyl Mercaptan | 1 |
| Di-tert-Butyl Disulfide | 3 |

It would appear to be excellent stock for recycle back to the process.

The distillation was continued at a pressure of 20 to 2 mm Hg absolute and a final kettle temperature of 310° F (154° C). The composite of this fraction, 326 g, had the following composition:

| | |
|---|---|
| Lights[1] | 0.1 |
| Unidentified | 3.6 |
| Di-tert-Butyl Disulfide | 94.2 |
| Di-tert-Butyl Trisulfide | 1.9 |
| Polysulfides | 0.2 |
| Total | 100.0 |

[1]Includes isopropanol and tert-butyl mercaptan. The yield was 91.6 mole percent based on the mercaptan charge.

The dry kettle contained 6 g solid sodium sulfide.

The water phase (736 g) from Run 7 was distilled to see how much disulfide and isopropanol it contained. Only 4 ml disulfide, about 1 mole percent, was recovered. In 240 ml water taken over, less than 3 percent was isopropanol. Thus, it appears that the water phase from the process can be discarded without appreciable loss of product or of solvent.

In a demonstration of the stepwise addition of reactants, Run 8 was made with initial addition of caustic as 50 percent solution in water, solvent, and sulfur. Then with the stirrer running, the mercaptan was charged from a dropping funnel over a period of 5 minutes from start to finish. The temperature at the start was 120° F (49° C) and at the end of the addition was 139° F (59° C). Heat was applied and the run was continued at the reflux temperature of 170° F (77° C). Samples of the organic phase were analyzed at 1, 16.5, and 25 hours reaction time with results shown in Table II. The data show that there was considerable mercaptan left unreacted even after 25 hours. Thus, under the conditions of this process using isopropanol-water solvent, sulfur addition should be deferred until the initial reaction between NaOH and mercaptan is virtually complete. The reason for this is not readily apparent unless competing reactions consumed part of the sulfur so that it was no longer available for oxidizing the mercaptan.

TABLE II

DISULFIDE BY THE SULFUR PROCESS IN ISOPROPANOL AND WATER

| | | Run 7 | | | | Run 8 | | |
|---|---|---|---|---|---|---|---|---|
| A. | Solvent, g | | | | | | | |
| | Water | 500 | | | | 500 | | |
| | Isopropanol | 500 | | | | 500 | | |
| B. | Charge | g | moles | | | g | moles | |
| | NaOH | 200 | 5.0 | | | 200 | 5.0 | |
| | tert-Butyl Mercaptan | 360 | 4.0 | | | 360 | 4.0 | |
| | Sulfur | 70.4 | 2.2 | | | 70.4 | 2.2 | |
| C. | Temperature °F | 155 – 170 | | | | 168 – 170 | | |
| | °C | 68.8 – 77 | | | | 75.4 – 77 | | |
| D. | Composition at hrs. | 2 | 4 | 8.5 | (1) | 1 | 16.5 | 25 |
| | Lights | 0.1 | tr | 0.1 | 0.1 | 0.1 | 0.1 | 0.1 |
| | Isopropanol | 56.3 | 61.8 | 63.5 | — | 52.5 | 54.6 | 60.3 |
| | tert-Butyl Mercaptan | 18.4 | 5.7 | 1.0 | — | 33.1 | 7.2 | 6.5 |
| | Unidentified | 2.8 | 1.8 | 1.5 | 3.6 | 6.2 | 9.3 | 4.1 |
| | Disulfide | 19.6 | 29.3 | 33.1 | 94.2 | 6.8 | 27.8 | 28.2 |
| | Trisulfide | 2.1 | 1.1 | 0.6 | 1.9 | 1.3 | 1.0 | 0.5 |
| | Polysulfides | 0.7 | 0.3 | 0.2 | 0.2 | — | tr | 0.5 |
| | Total | 100.0 | 100.0 | 100.0 | 100.0 | 100.0 | 100.0 | 100.0 |
| E. | Organic Phase Recovered, g | | | 863 | | | | |
| F. | Disulfide by Distillation, g | | | 326 | | | | |
| G. | Yield, Mole Percent | | | | | | | 91.6 |

[1]Recovered by distillation of the organic phase in a one-plate vacuum distillation apparatus. The kettle contained 5g Na$_2$S in form of dry crystals at end of the distillation.

EXAMPLE VIII

In order to test what would result if all the ingredients were charged to the reactor simultaneously, a run was made. Solvent [isopropanol and water (50/50)], caustic (pellets), mercaptan, and sulfur all were charged with the stirrer off. With the temperature at 110° F (43° C), the stirrer was started cautiously. However, in less than 10 seconds, the temperature went to 160° F (71° C) and the stopper blew out of the reactor and part of the contents were lost. The run was discontinued.

In view of the foregoing runs, it has been observed that only a slight temperature rise on addition of mercaptan to the NaOH, isopropanol-water charge occurs, but that a run-away reaction was started when all of the ingredients were present initially. Thus, the instant two-stage process has improved controllability.

EXAMPLE IX

The solvent charge for this run was 800 g isopropanol and 200 g water to determine if the reaction rate could be improved using excess isopropanol. The other components charged and the procedure were the same as in previous Example VII. In this run, however, the mercaptide slurry was too thick to stir, and 200 g more isopropanol was added; and there were other problems. On cooling overnight, the mixture set up solid, and all of the solids did not go back into solution at the reflux temperature until 300 g water was added. This put the solids in solution, and refluxing was continued for 6.5 hours (total reflux time 9 hours).

The crude product was transferred to a separatory funnel; phase separation was excellent. The organic phase was flash distilled to a kettle temperature of 250° F (121° C) at one atmosphere. The kettle product, 337 g, was then washed twice with 250 ml water in each wash. The organic phase, 302 g, was drawn off; it was quite cloudy. It was then filtered over Drierite, but this failed to remove much of the material producing the cloud. The washed product contained 96.1 weight percent disulfide, however.

Conclusions drawn from this part of the work were that no advantage could be seen in using more isopropanol in the solvent. Additionally, it does not appear that water washing is a satisfactory way to clean up the disulfide product.

EXAMPLE X

Other Solvents: Water, ammonium hydroxide, and 2-pyrrolidone were also tried as reaction media. The data are shown in Table III. In all of these runs, the primary products were tri- and polysulfides. This was surprising only in the case of 2-pyrrolidone; this solvent was expected to be as good as NMP, but it definitely was not. The reason is not known.

TABLE III

| Disulfides by the Sulfur Process With Other Reaction Media | | | |
|---|---|---|---|
| Run No. | 9 | 10 | 11 |
| A. Solvent, g | | | |
| Water | 1200 | — | 500 |
| NH₄OH | — | 625 | — |
| 2-Pyrrolidone | — | — | 500 |
| B. Conditions | | | |
| Temperature, °F | 160–182 | 74–142 | 165–190 |
| °C | 71–83.1 | 23.3–61.1 | 73.8–88 |
| React.Time,hrs. | 3.0 | 3.0 | 4.0 |
| C. Charge, moles | | | |
| NaOH | 5.0 | 5.0⁽¹⁾ | 5.0 |
| t-Butyl Mercaptan | 4.0 | 4.0 | 4.0 |
| Sulfur | 2.0 | 2.0 | 2.2 |
| D. Recovery, g | 172 | —⁽²⁾ | —⁽²⁾ |
| Mole percent | 49 | — | — |
| E. Composition of Crude, Wt. % | | | |
| Lights | 0.1 | 0.1 | 0.2 |
| t-Butyl Mercaptan | 2.0 | 0.6 | 56.6 |
| Unidentified | 4.5 | 0.8 | 0.6 |
| Di-tert-Butyl Disulfide | 23.7 | 11.0 | 5.3 |
| Unidentified | 3.7 | 0.5 | — |
| Di-tert-Butyl Trisulfide | 65.8 | 32.7 | 37.0 |
| Polysulfides | 0.2 | 54.3 | 0.3 |
| Total | 100.0 | 100.0 | 100.0 |

⁽¹⁾Five moles NH₄OH was the charge. No NaOH used in this run.
⁽²⁾Did not recover the organic phase.

The above-described examples demonstrate that good quality disulfide can be made in yields of 85–90+ mole percent with NMP-water or isopropanol-water as reaction medium with sulfur as the oxidizing agent. NMP-water would be the preferred solvent except for the problem of recovering the NMP. Isopropanol-water works equally as well as solvent except for the reaction time which is several orders of magnitude longer. The reaction can undoubtedly be speeded up, however, by operation at a few pounds pressure.

Timewise, NMP/water is a preferable medium and suitable for a batch process where solvent recovery can be carried out separately. A very efficient continuous process can be provided for an isopropanol-water process which operates below 200° F at atmospheric pressure and in which a simple distillation step can recover and recycle the solvent alcohol.

Thus, the above-described examples demonstrate various advantages for the instant two-stage process, namely, lower reation temperatures, shorter reaction times, no evolution of H₂S, and recovery of high purity product without complex fractional distillation or other complicated recovery treatments.

I claim:
1. An improved process for the production of disulfides which comprises the steps of:
   I. reacting (a) at least one mercaptan with (b) at least one alkali metal hydroxide in (c) a reaction medium comprising N-methylpyrrolidone, N-methylpyrrolidone/water, and isopropanol/water under conditions which produce an alkali metal mercaptide and
   II. adding sufficient sulfur to the reaction mass of step (I) containing said alkali metal mercaptide to oxidize the mercaptide to the disulfide and heating the reaction mass containing the added sulfur to a temperature and for a period of time sufficient to cause the reaction product to contain a substantial preponderance of disulfide.
2. A process according to claim 1 wherein the mercaptan is an aliphatic or cycloaliphatic mercaptan having the general formula RSH in which R is an alkyl or cycloalkyl radical having from 1 to 20 carbon atoms.
3. A process according to claim 1 wherein the reaction medium is N-methylpyrrolidone and the amount of reaction medium present is sufficient to keep the weight percent solids below about 35 percent.
4. A process according to claim 1 wherein said reaction medium is a 50/50 weight percent mixture of N-methylpyrrolidone and water and the amount of reaction medium present is sufficient to keep the weight percent solids below about 35 percent.
5. A process according to claim 1 wherein the reaction medium is about a 50/50 weight percent mixture of isopropanol and water and the amount of solvent present is sufficient to keep the weight percent solids below about 35 percent.
6. A process according to claim 1 wherein the temperature of reaction is about 65° to about 350° F (18.3°–177° C) and the time of reaction is in the range of about 1 to about 3 hours and the pressure is in the range of about 0 to about 150 psig.
7. A process according to claim 1 wherein the mercaptan is tertiary-butyl mercaptan and the disulfide is di-tert-butyl disulfide and the alkali metal hydroxide is sodium hydroxide.
8. A process according to claim 1 wherein said reacting is carried out at the reflux temperature.

* * * * *